United States Patent
Kim et al.

(10) Patent No.: US 8,208,985 B2
(45) Date of Patent: Jun. 26, 2012

(54) METHOD AND SENSOR MEASURING SKIN IMPEDANCE

(75) Inventors: Hong Sig Kim, Yongin-si (KR); Woo Young Jang, Yongin-si (KR); Jae Chan Park, Yongin-si (KR); Jeong Je Park, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1080 days.

(21) Appl. No.: 11/806,839

(22) Filed: Jun. 4, 2007

(65) Prior Publication Data

US 2008/0033315 A1 Feb. 7, 2008

(30) Foreign Application Priority Data

Jun. 9, 2006 (KR) .................. 10-2006-0052054

(51) Int. Cl.
*A61B 5/04* (2006.01)
*A61B 5/05* (2006.01)
(52) U.S. Cl. .................. 600/393; 600/386; 600/547
(58) Field of Classification Search .................. 600/393, 600/547, 386
See application file for complete search history.

(56) References Cited

U.S. PATENT DOCUMENTS

| | | | | |
|---|---|---|---|---|
| 4,082,087 A | * | 4/1978 | Howson | 600/391 |
| 4,275,743 A | * | 6/1981 | Hjort | 600/544 |
| 4,448,199 A | * | 5/1984 | Schmid | 600/393 |
| 5,353,802 A | * | 10/1994 | Ollmar | 600/547 |
| 5,738,107 A | | 4/1998 | Martiensen et al. | |
| 5,935,077 A | | 8/1999 | Ogle | |
| 6,186,962 B1 | | 2/2001 | Lloyd et al. | |
| 7,738,939 B2 | * | 6/2010 | Hallin | 600/393 |
| 2005/0277822 A1 | * | 12/2005 | Manabe et al. | 600/393 |

FOREIGN PATENT DOCUMENTS

| | | |
|---|---|---|
| EP | 1384436 A2 | 1/2004 |
| GB | 2415051 A | 12/2005 |
| JP | 9-215667 | 8/1997 |
| JP | 10-075936 | 3/1998 |
| JP | 2001-046344 | 2/2001 |
| JP | 2003-169787 | 6/2003 |
| JP | 2004-057704 | 2/2004 |
| KR | 10-2005-0026791 | 3/2005 |
| WO | WO 96/10951 | 4/1996 |

OTHER PUBLICATIONS

Japanese Office Action for corresponding Japanese Patent Application No. 2007-147145 dated May 25, 2010 (2 pgs).
European Search Report for corresponding European Application No. 07109807.3 dated Sep. 27, 2007 (4 pgs) (in English).

* cited by examiner

*Primary Examiner* — Lee Cohen
(74) *Attorney, Agent, or Firm* — Staas & Halsey LLP

(57) ABSTRACT

A sensor measuring skin impedance includes a reference electrode, a current carrying electrode, and a measuring electrode for measuring impedance for current flowing between the reference electrode and the current carrying electrode. The measuring electrode is recessed with respect to the reference electrode and the current carrying electrode, allowing the measuring electrode to make contact with a user's skin after the reference electrode and current carrying electrode make contact, resulting in greater measurement accuracy.

13 Claims, 11 Drawing Sheets

METHOD AND SENSOR MEASURING SKIN IMPEDANCE

CROSS-REFERENCE TO RELATED APPLICATIONS

This application claims the benefit of Korean Patent Application No. 10-2006-0052054, filed on Jun. 9, 2006, in the Korean Intellectual Property Office, the disclosure of which is incorporated herein by reference.

BACKGROUND

1. Field

One or more embodiments of the present invention relate to a method and sensor measuring skin impedance, and more particularly, to a method and sensor measuring skin impedance with improved accuracy using a measuring (M) electrode slightly recessed with respect to a reference (R) electrode and a current carrying (C) electrode causing the M electrode to makes contact with a user's skin after the R electrode and the C electrode.

2. Description of the Related Art

As more and more people become interested in beauty, interest in skin care has also increased. People also need to protect their skin from ultraviolet rays, which have become stronger due to the destruction of the ozone layer, and from various types of pollution. Therefore, a desire for a healthy skin relates not only to beauty-related products, but also to the growth of medical-related products.

Measuring skin moisture is a generally accepted method for self-diagnosing skin health. Moisture content in skin can be measured using a portable device, which may be implemented using skin impedance measurement techniques.

For example, U.S. Pat. No. 5,738,107 "Measurement of Moisture Content in Skin" discusses a device for determining relative skin moisture by measuring skin impedance. Here relative skin moisture is determined by measuring susceptance using an alternating current (AC) component of admittance, for three electrodes using a 50 KHz sinusoidal wave.

FIG. 1A illustrates a sensor and FIG. 1B illustrates a circuit for measuring skin impedance.

As illustrated in FIG. 1A, a sensor measuring skin impedance may include an R electrode, a C electrode, and an M electrode. When the sensor, having three electrodes, makes contact with a user's skin, a current begins to flow between the R electrode and the C electrode, through the skin. Here, the M electrode may measure impedance by measuring the current flowing between the R electrode and the C electrode.

In this case, noise may occur depending on how the electrodes make contact with the skin. Specifically, referring to a circuit illustrated in FIG. 1B, after power is supplied to an operational amplifier (Op Amp) 100, a voltage at pC is momentarily charged by an offset current to +Vcc or −Vcc. When the user's skin makes contact with the C and M electrodes, impedance for the skin becomes high due to a large amount of current that momentarily flows. However, when the R electrode makes contacts with the user's skin, the voltage on the C electrode returns to an original stable state.

Namely, when the R and C electrodes initially contact with the user's skin, subsequently the M electrode contacts with the user's skin, the impedance can be correctly measured. Conversely, when the R and M electrodes initially contact with the user's skin, subsequently the C electrode contacts with the user's skin, or when the C and M electrodes initially contact with the user's skin, subsequently the R electrode contacts with the user's skin, the impedance becomes abnormally high so that an error as illustrated in FIG. 2B occurs.

FIG. 2A is a graph illustrating when the impedance is normally measured, i.e. the R and C electrodes initially contact with the user's skin, subsequently the M electrode contacts with the user's skin. FIG. 2B is a graph illustrating when the impedance is abnormally measured, i.e. when the C and M electrodes initially contact with the user's skin, subsequently the R electrode contacts with the user's skin. In the above graphs, an x axis indicates times, i.e. seconds, and a y axis indicates impedance values.

As illustrated in FIG. 2A, when the impedance is correctly measured, a stable impedance value may be measured after approximately 1.3 seconds. Therefore, the impedance may be accurately measured since variations of the value are less for every subsequent measurement. Conversely, as illustrated in FIG. 2B, since an error has occurred at the beginning of the measurement, a stable impedance value may not be measured until after approximately 2.5 seconds to 4.1 seconds. Therefore, the impedance may not be accurately measured because, depending upon the measurement cycle, variations of the value are great in subsequent measurements.

To solve the above-described problems, one or more embodiments of the present invention disclose a method and sensor measuring skin impedance that can instantly and accurately measure the impedance of the user's skin with improved accuracy.

SUMMARY

An aspect of one or more embodiments of the present invention provides a method and sensor measuring skin impedance having a measuring electrode (M) that is slightly recessed with respect to a reference electrode (R) and a current carrying (C) electrode, allowing the M electrode to make contact with a user's skin after the R electrode and C electrode make contact, resulting in greater measurement accuracy.

An aspect of one or more embodiments of the present invention also provides a method and sensor measuring skin impedance which can easily and accurately measure skin impedance of a user by establishing an elastic element or a seesaw arm member connected to an R electrode and a C electrode.

Additional aspects and/or advantages of the invention will be set forth in part in the description which follows and, in part, will be apparent from the description, or may be learned by practice of the invention.

To achieve at least the above and/or other aspects and advantages, the one or more embodiments include a sensor measuring skin impedance including a reference (R) electrode and a current carrying (C) electrode, and a measuring (M) electrode, recessed with respect to the R electrode and the C electrode, to measure impedance for a current flowing between the R electrode and the C electrode, across a skin surface contacted by the M electrode after the R electrode and the C electrode.

To achieve at least the above and/or other aspects and advantages, one or more embodiments of the present invention include a sensor measuring skin impedance including an R electrode and a C electrode to make contact with a skin, an elastic element connected to the R electrode and the C electrode, the elastic element to compress according to a pressure exerted upon the R electrode and the C electrode, and an M electrode, slightly recessed with respect to the R electrode and the C electrode, to measure impedance for a current flowing between the R electrode and the C electrode across the skin.

To achieve at least the above and/or other aspects and advantages, one or more embodiments of the present invention include a sensor measuring skin impedance including an R electrode and a C electrode to make contact with a user's skin, an M electrode, slightly recessed with respect to the R electrode and the C electrode, and a seesaw arm member to connect to the R electrode, the C electrode, and the M electrode, wherein the seesaw arm member includes a first elastic element to perform an elastic movement according to displacement of the R electrode and the C electrode and a second elastic element, connected to the M electrode, to perform an elastic movement according to displacement of the first elastic element, to enable the R electrode and the C electrode to make contact with the skin before the M electrode makes contact with the skin.

To achieve at least the above and/or other aspects and advantages, one or more embodiments of the present invention include a sensor measuring skin impedance including an R electrode and a C electrode to make contact with a skin, an M electrode, recessed with respect to the R electrode and the C electrode, and an elastic element connected to the R electrode and the C electrode, the elastic element being compressed when pressure is applied to the R electrode and the C electrode, the compression causing the M electrode to no longer be recessed with respect to the R electrode and the C electrode, enabling the M electrode to make contact with the user's skin after the R electrode and the C electrode.

To achieve at least the above and/or other aspects and advantages, one or more embodiments of the present invention include method for measuring skin impedance with a sensor having an M electrode recessed with respect to an R electrode and a C electrode, and an elastic element to connect the R electrode and the C electrode, the method comprising applying the sensor to a surface of a skin, exerting pressure on the sensor to compress the elastic element, until the M electrode is no longer recessed with respect to the R electrode and the C electrode, to control contact of all three electrodes with a skin surface.

BRIEF DESCRIPTION OF THE DRAWING

These and/or other aspects and advantages of the invention will become apparent and more readily appreciated from the following description of the embodiments, taken in conjunction with the accompanying drawings of which.

DETAILED DESCRIPTION OF EMBODIMENTS

Figure 1A:
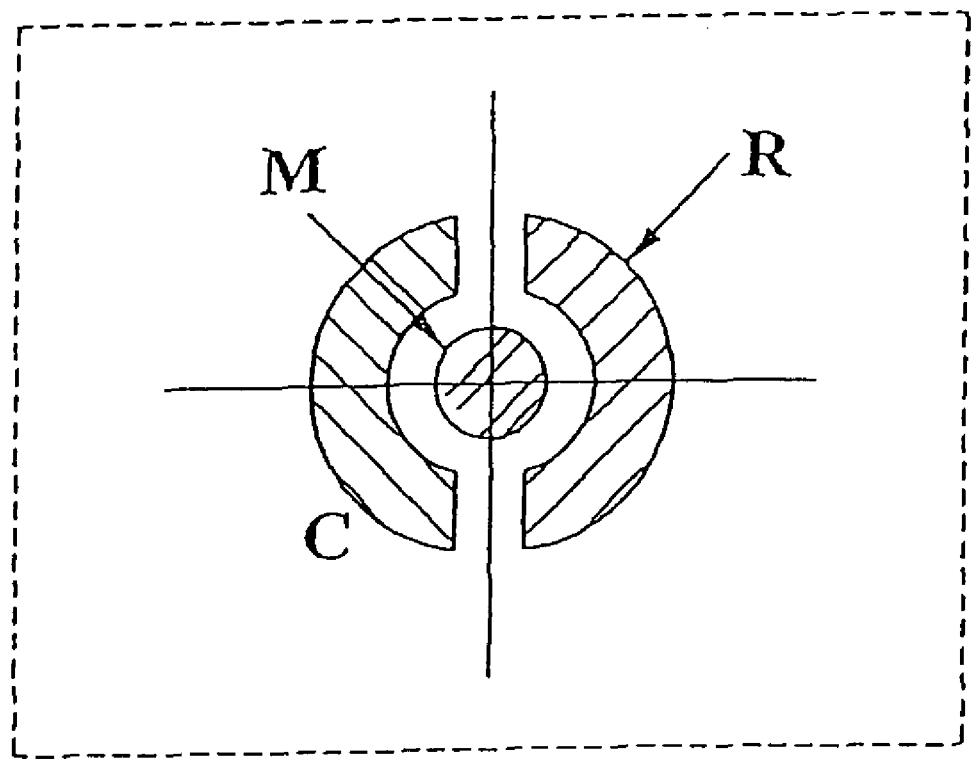
FIGS. 1A and 1B illustrate a conventional sensor and a circuit of a skin impedance measurement device, respectively.
Figure 1B:
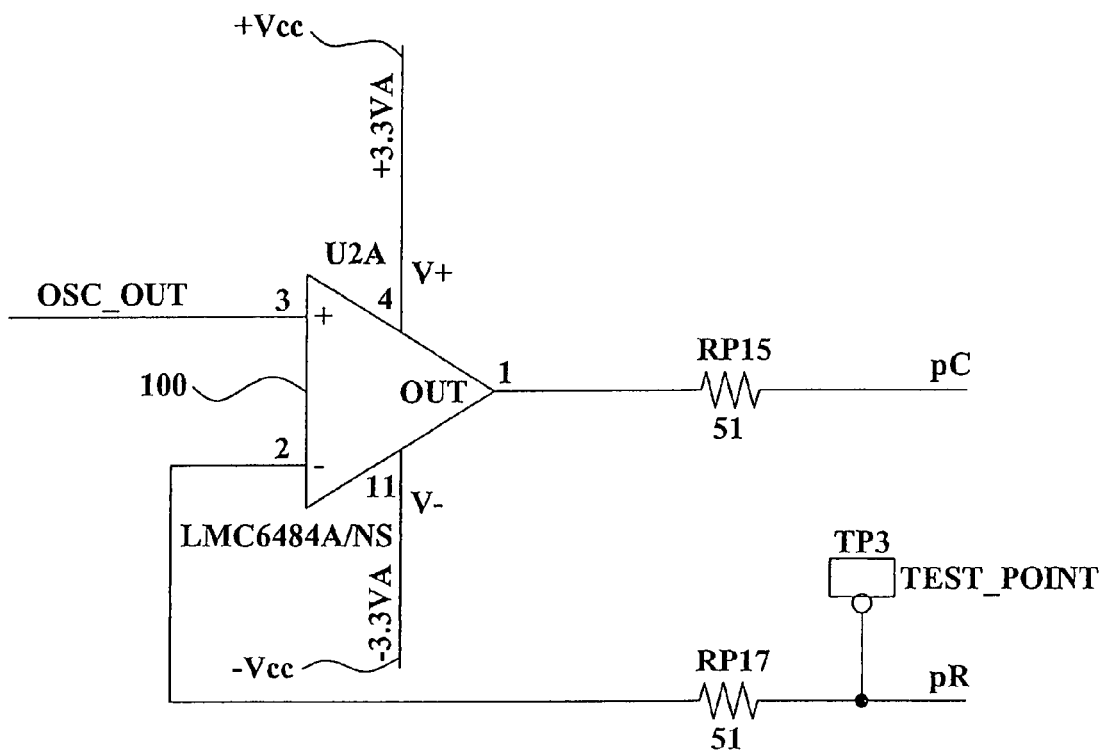
Figure 2A:
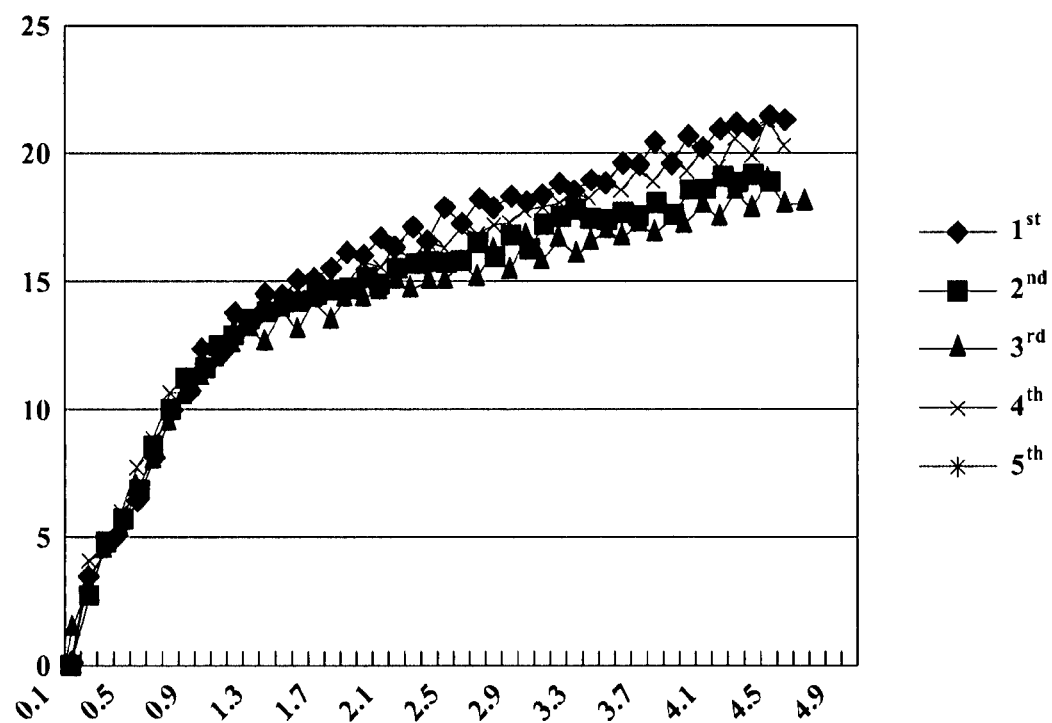
FIGS. 2A and 2B illustrate example conventional skin impedance measurement results
Figure 2B:
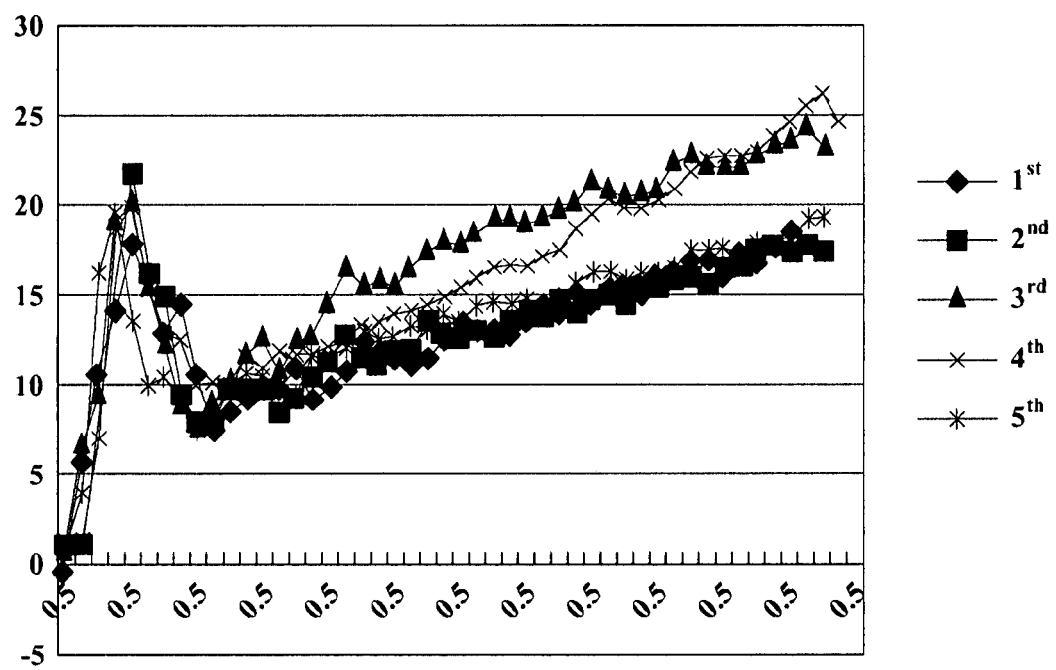

Reference will now be made in detail to one or more embodiments of the present invention, examples of which are illustrated in the accompanying drawings, wherein like reference numerals refer to the like elements throughout. One or more embodiments are described below in order to explain the present invention by referring to the figures.

A sensor measuring skin impedance according to one or more embodiments of the present invention may be embodied as any portable device, for example, including, but not limited to, a mobile communication terminal, a personal digital assistance (PDA), a portable game device, an MP3 player, a portable multimedia player (PMP), a Digital Multimedia Broadcasting (DMB) terminal, and a notebook device. Namely, the method and sensor measuring skin impedance may be embodied as a partial configuration of the portable devices or may be embodied as a stand-alone device.

Figure 3:
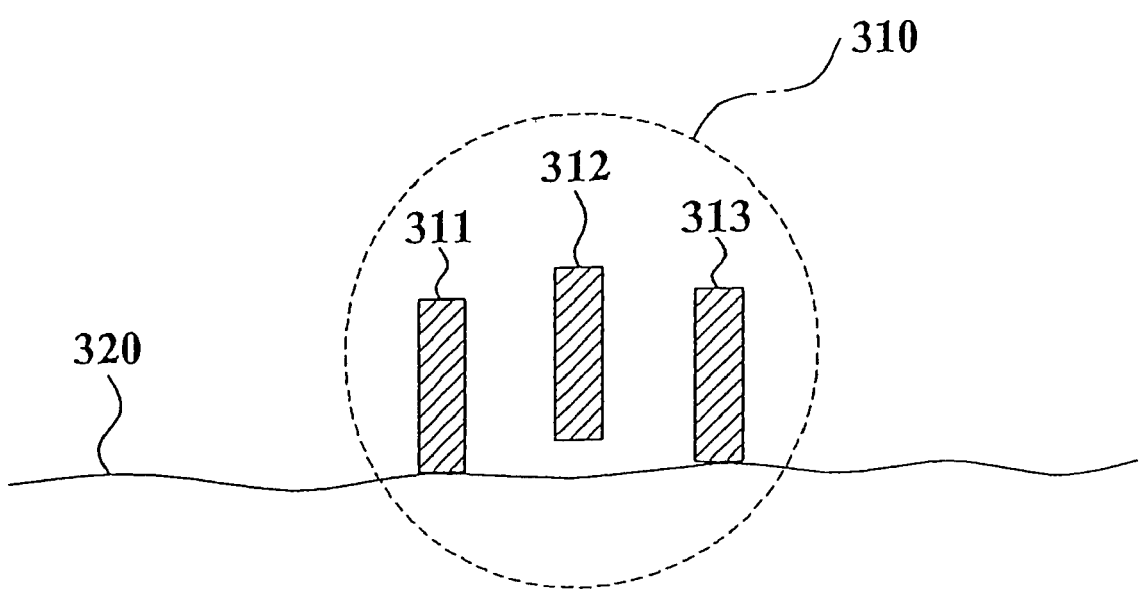
FIG. 3 illustrates a sensor method for measuring skin impedance, according to one or more embodiments of the present invention.
Figure 4A:
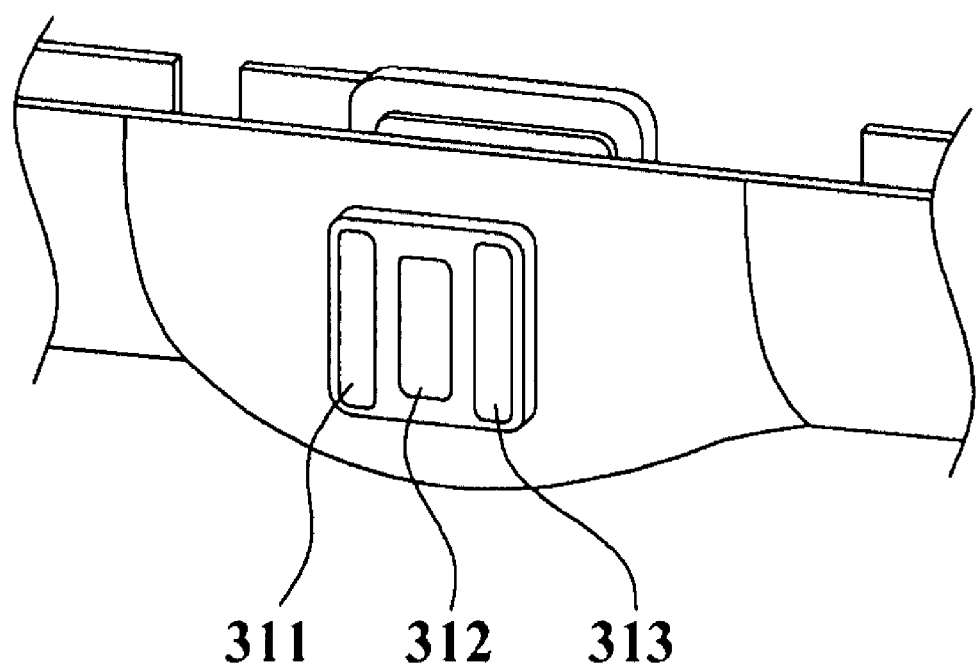
FIGS. 4A and 4B illustrate a sensor measuring skin impedance, according to one or more embodiments of the present invention.
Figure 4B:
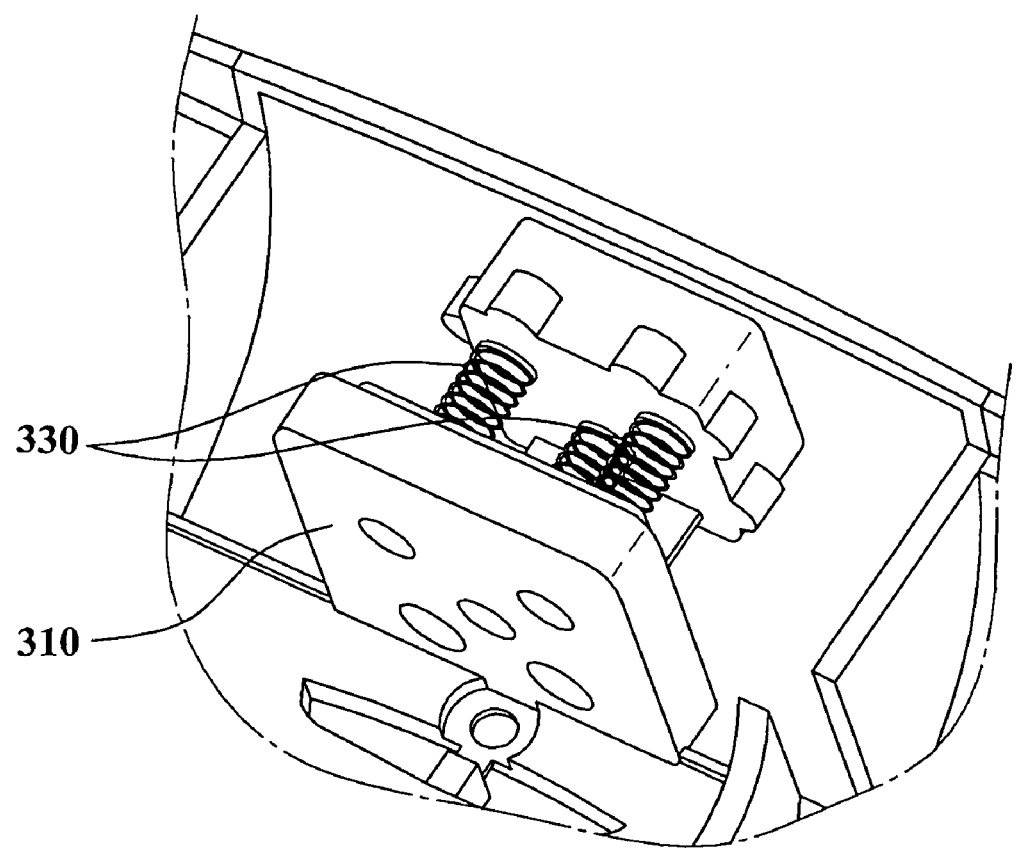

FIG. 3 illustrates a sensor and method for measuring skin impedance, according to one or more embodiments of the present invention. FIGS. 4A and 4B similarly illustrate a sensor measuring skin impedance, according to one or more embodiments of the present invention. The sensor method for measuring skin impedance may be explained by reference to sensor 310, and may include, for example, an M electrode 312 that is recessed with respect to an R electrode 311 and a C electrode 313.

As described above, the electrodes 311, 312 and 313 may include operations and configurations for each electrode according to the U.S. Pat. No. 5,738,107 "Measurement of Moisture Content in Skin", which is herein incorporated by reference, noting that alternative embodiments of the present invention are equally available.

Specifically, as illustrated in FIG. 3, when the sensor 310 contacts a user's skin, the M electrode 312 may be slightly recessed, for example by an indentation, with respect to the R electrode 311 and the C electrode 313. This allows the M electrode 312 to make contact with the skin after the R electrode 311 and the C electrode 313 have made contact with the skin.

In this case, when the M electrode 312 is recessed with respect to the R electrode 311 and the C electrode 313, the M electrode 312 may make contact with the user's skin 320 after the R electrode 311 and the C electrode 313 have made contact because the skin 320 has elasticity. Namely, the R electrode 311 and the C electrode 313 exert pressure on the skin when the sensor makes contact with the skin. Specifically, when the user's skin 320 receives pressure exerted by the R electrode 311 and the C electrode 313, the user's skin 320 located right below the R electrode 312 becomes protruded, due to the elasticity of the skin 320 and the received pressure. This allows the M electrode 312 to make contact with the skin 320.

Accordingly, such a recess of the M electrode 312 with respect to the R electrode 311 and the C electrode 313 may be designed to fall within a range, allowing for the elasticity of the skin 320, within which range the M electrode 312 may contact the skin 320 after the R electrode 311 and the C electrode 313 have made contact with the skin 320. Specifically, in an embodiment, the recess may be designed within a range of approximately 1 mm to 2 mm.

According to one or more embodiments of the sensor 310, when the user places the sensor 310 in contact with the skin 320, the R electrode 311 and the C electrode 313 initially make contact with the skin 320. Subsequently, as the user applies pressure to the skin via the R electrode 311 and the C electrode 313, a portion of the skin 320 located between the R electrode 311, and the C electrode 313 receives the pressure. The pressure may allow a portion of the skin 320 located directly below the M electrode 312 to make contact with the M electrode 312. Upon the M electrode's 312 making contact with the skin, a weak current may begin to flow between the R electrode 311 and the C electrode 313 through the skin 320, and the skin impedance may be measure using the M electrode 312.

In one embodiment, each of electrodes 311, 312, and 313 of the sensor 310 may be shaped like a bar. For example, when the sensor 310 is embodied as a partial configuration of a portable device, it may be desirable for the sensor 310 to be miniaturized. Miniaturizing the sensor 310 may also cause the cross-section of the M electrode 312, for making contact with the skin 320, to be miniaturized. When the cross-section of the M electrode 312 is miniaturized, the available surface area for measuring an electrical signal decreases, potentially leading to an issue of increased electrical noise.

As illustrated in FIG. 4A, in order to maintain the cross-section of the M electrode 312 to a predetermined size while miniaturizing the electrodes of the sensor 310, the electrodes 311, 312, and 313 may be formed in a bar shape.

As describe above, when electrodes 311, 312 and 313 are formed in a bar shape, the cross-section of the electrodes 311, 312 and 313 making contact with the skin 320 can be constantly maintained to be greater than a predetermined size. Thus, accuracy in measuring skin impedance may be improved when a user's skin has less moisture.

Also, forming the electrodes 311, 312, and 313 in a bar shape may improve accuracy for measuring skin impedance because the cross-sections of the electrodes 311, 312, and 313 are able to sufficiently make contact with the skin 320, even when each of electrodes 311, 312, and 313 can not make sufficient contact with the skin 320 due to undulations and elasticity, e.g. a hand and a cheek.

Also, as illustrated in FIG. 4B, the sensor 310, according to one or more embodiments of the present invention, may include an elastic element, e.g., one or more springs 330, for miniaturization of the sensor, and for controlling measuring pressure and a height of the sensor 310.

Each of the electrodes 311, 312, and 313 of the sensor 310 may be embodied in various forms capable of maximizing the cross-section making contact with the skin 320 when the electrodes are miniaturized.

According to one or more embodiments of the present invention, the sensor measuring skin impedance 310 includes the M electrode 312, which may be slightly recessed with respect to the R electrode 311 and the C electrode 313, as described above. Namely, in one or more embodiments of the present invention, the M electrode 312 is located relatively lower than the R electrode 311 and the C electrode 313.

Figure 5A:
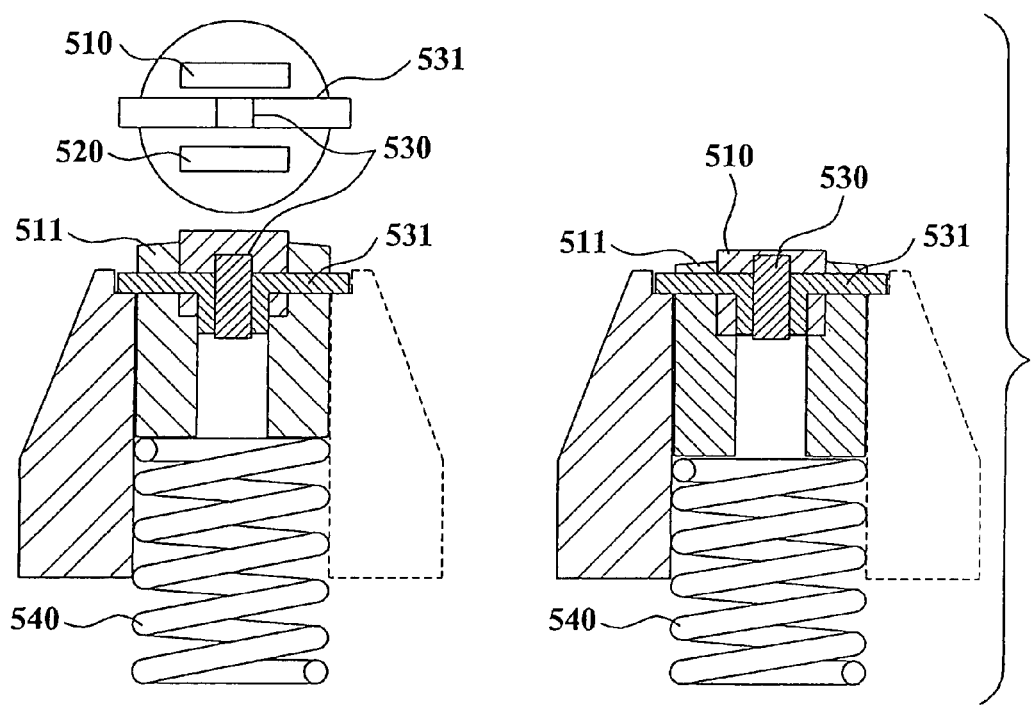
FIGS. 5A and 5B illustrate a sensor measuring skin impedance, according to one or more embodiments of the present invention.
Figure 5B:
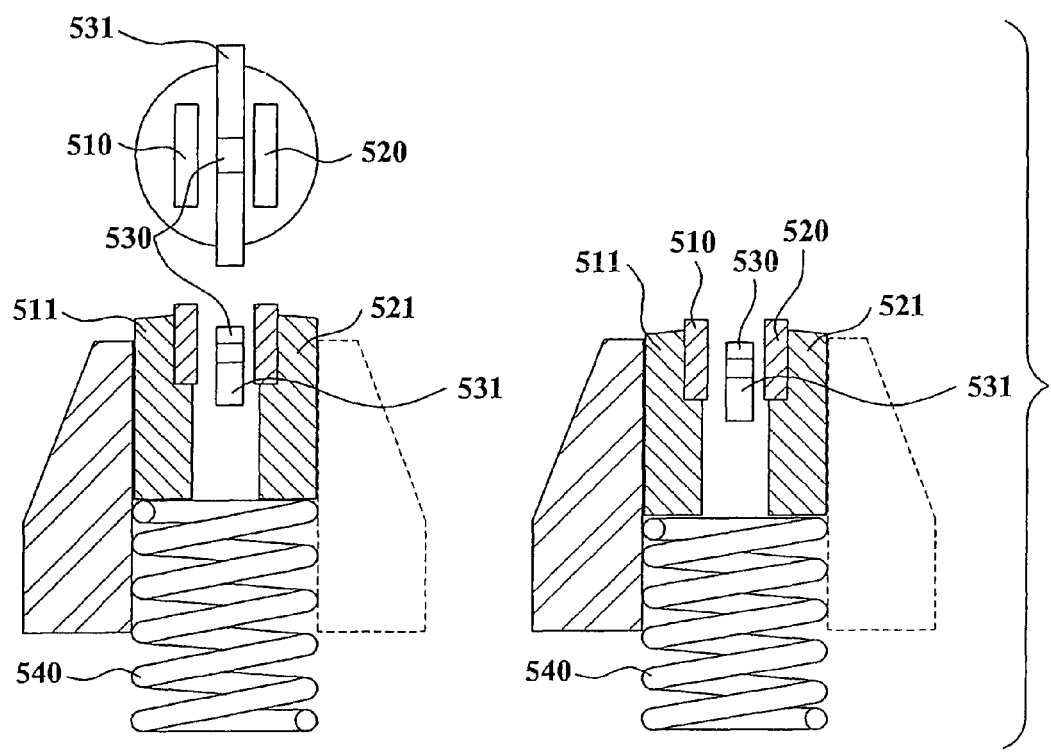
Figure 6:
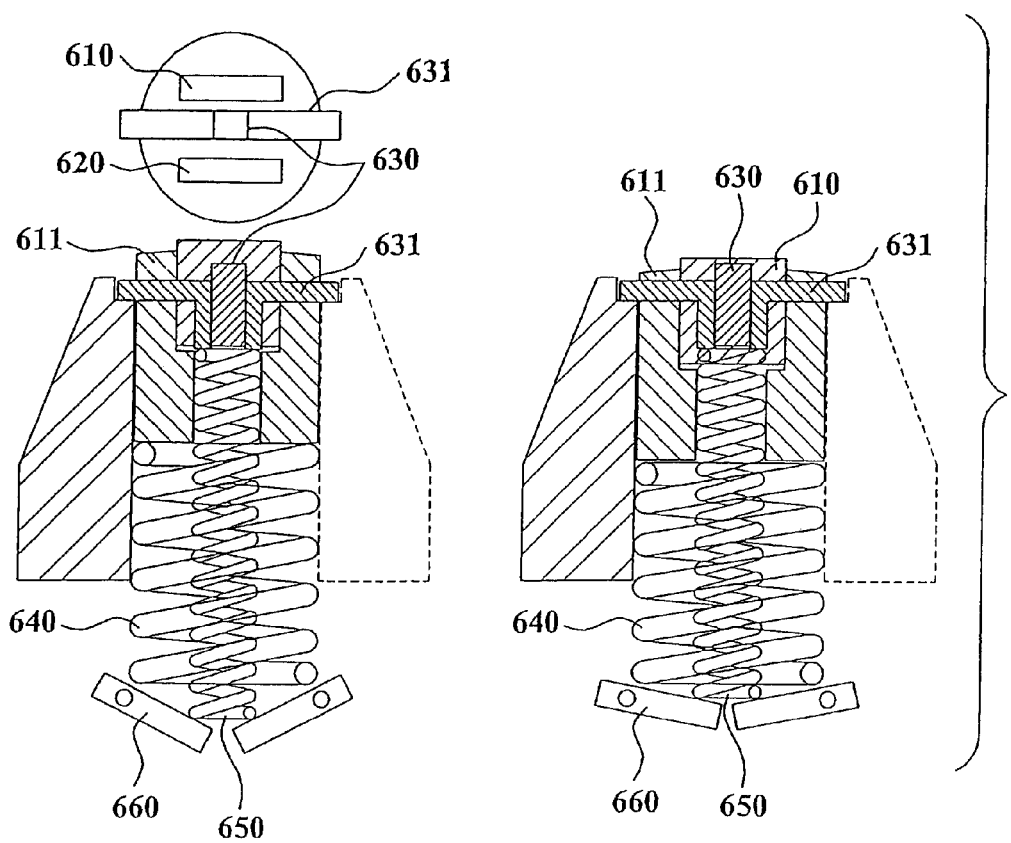
FIG. 6 is illustrates a structure of a sensor measuring skin impedance according to one or more embodiments of the present invention.

As illustrated in FIGS. 5A, 5B, and 6, one or more embodiments of the present invention include a sensor, and a corresponding method, that may include an M electrode that is slightly recessed with respect to an R electrode and a C electrode. In one embodiment, the R electrode, the C electrode and the M electrode may move by operation of an elastic element, for example, a seesaw arm member.

FIGS. 5A and 5B illustrate a sensor and method for measuring skin impedance, according to one or more embodiments of the present invention. FIG. 5A is a front-view illustrating the sensor 310 for measuring skin impedance, and FIG. 5B is a cross-sectional view illustrating the sensor 310 for measuring skin impedance.

The sensor for measuring skin impedance may include, for example, an R electrode 510, a C electrode 520, an M electrode 530, an elastic element 540, an R electrode support 511, a C electrode support 521 and an M electrode support 531.

The R electrode 510 may be supported by the R electrode support 511, the C electrode 520 may be supported by the C electrode support 521, and the M electrode 530 may be supported by the M electrode support 531. Also, the R electrode support 511 and the C electrode support 521 may be connected with the elastic element 540. In this case, as an example only, the M electrode support 531 need not be connected to the elastic element 540.

Also, similar to the sensor illustrated in FIG. 3, in one or more embodiments of the present invention the M electrode 530 may be slightly recessed with respect to the R electrode 510 and the C electrode 520, with respect to the skin to be measured.

When the sensor makes contact with the user's skin to measure skin impedance, the R electrode 510 and the C electrode 520 may initially make contact with the skin due to the recess of the M electrode 530. Upon the initial contact, the R electrode 510 and the C electrode 520 receive pressure exerted by the user on the sensor. The pressure may be delivered to the R electrode support 511 and the C electrode support 521. The pressure may then be delivered to the elastic element 540. The elastic element 540 may, thus, become compressed in proportion to the pressure.

As the elastic element 540 becomes compressed, the R electrode support 511 and the C electrode support 521 may move in the direction of compression of the elastic element 540. Accordingly, the R electrode 510 and the C electrode 520 may also move towards the compression direction. Specifically, as illustrated in FIG. 5A, the R electrode 510 and the C electrode 520 move in a relatively downward direction, i.e., in the direction of compression of the elastic element 540.

Accordingly, as the R electrode 510 and the C electrode 520 move in a downward direction, the M electrode 530 may make contact with the user's skin. When the M electrode 530 makes contact with the skin, impedance may be measured via the skin by measuring a current flowing between the R electrode 510 and the C electrode 520.

As described above, according to one or more embodiments of the present invention, accuracy in measuring skin impedance may be improved by slightly recessing the M electrode 530 with respect to the R electrode 510 and the C electrode 520, and by connecting the elastic element 540 to the R electrode 510 and the C electrode 520. After the R electrode 510 and the C electrode 520 make contact with the skin, the R electrode 510 and the C electrode 520 may move in the direction of compression of the elastic element 540, allowing the M electrode 530 to subsequently make contact with the skin.

FIG. 6 illustrates a sensor and method for measuring skin impedance, according to one or more embodiments of the present invention.

The sensor may include, for example, an R electrode 610, a C electrode 620, an M electrode 630, a first elastic element 640, a second elastic element 650, a seesaw arm 660, an R electrode support 611, a C electrode support (not illustrated), and an M electrode support 631. The first elastic element 640, the second elastic element 650, the seesaw arm 660, the R electrode support 611, the C electrode support and the M electrode support 631 may be embodied as a single seesaw arm member, as an example only, noting that alternative embodiments are equally available.

The R electrode 610 may be supported by the R electrode support 611, the C electrode 620 may be supported by the C electrode support, and the M electrode 630 may be supported by the M electrode support 631, for example. In one embodiment, the R electrode support 611 and the C electrode support may be connected to the first elastic element 640, the M electrode support 631 may be connected to the second elastic element 650, and/or the seesaw arm 660 may be embodied as a pair, with an outer edge of the seesaw arm 660 in contact with the first elastic element 640, and an inner edge of the seesaw arm 660 in contact with the second elastic element 650, for example.

The M electrode 630 of the sensor according to one or more embodiments of the present invention may be slightly recessed with respect to the R electrode 610 and the C electrode 620, with respect to the skin to be measured.

When a user places the sensor in contact with the skin 320 to measure skin impedance, the R electrode 610 and the C electrode 620 may make initial contact with the skin due to the recessed nature of the M electrode 630. The R electrode 610 and the C electrode 620, upon contact with the skin 320, receive pressure exerted by the user on the sensor. The pressure may be delivered to the R electrode support 611 and the C electrode support. The pressure delivered to the R electrode support 611 and the C electrode 631 may be delivered via the first elastic element 640.

The first elastic element 640 transfers the delivered pressure to the outer edge of the seesaw arm 660. When the pressure is transferred to the outer edge of the seesaw arm 660, the seesaw arm 660 may perform an oscillating motion to deliver pressure to the second elastic element 650 through the inner edge of the seesaw arm 660.

Subsequently, the second elastic element 650 may compress to transfer pressure to the M electrode support 631 via the pressure from the seesaw arm 660, and consequently deliver the pressure to the M electrode 630.

Accordingly, the M electrode 630 may be moved by the delivered pressure in the compression direction of the second elastic element 650, i.e. in an upward direction in FIG. 6, so as to make contact with the user's skin.

Namely, when the sensor makes contact with the user's skin, the R electrode 610 and the C electrode 620 may move in the direction of compression of the first elastic element 640, i.e. in a downward direction in FIG. 6, and the M electrode 630 may move in the direction of compression of the second elastic element 650, i.e. in an upward direction in FIG. 6. Therefore, the M electrode 630 may make contact with the skin after the R electrode 610 and the C electrode 620 make contact with the skin.

As described above, according to one or more embodiments of the present invention, accuracy in measuring skin impedance may be improved because the M electrode 630 may move to make contact with the user's skin via the second elastic element 660 according to the oscillating motion of the seesaw arm 660.

As illustrated in FIGS. 5A, 5B, and 6, the R, C and M electrodes of the sensor measuring skin impedance according to one or more embodiments of the present invention may again be formed in a bar shape, similar to each of the electrodes 311, 312, and 313 of FIG. 3.

Figure 7:
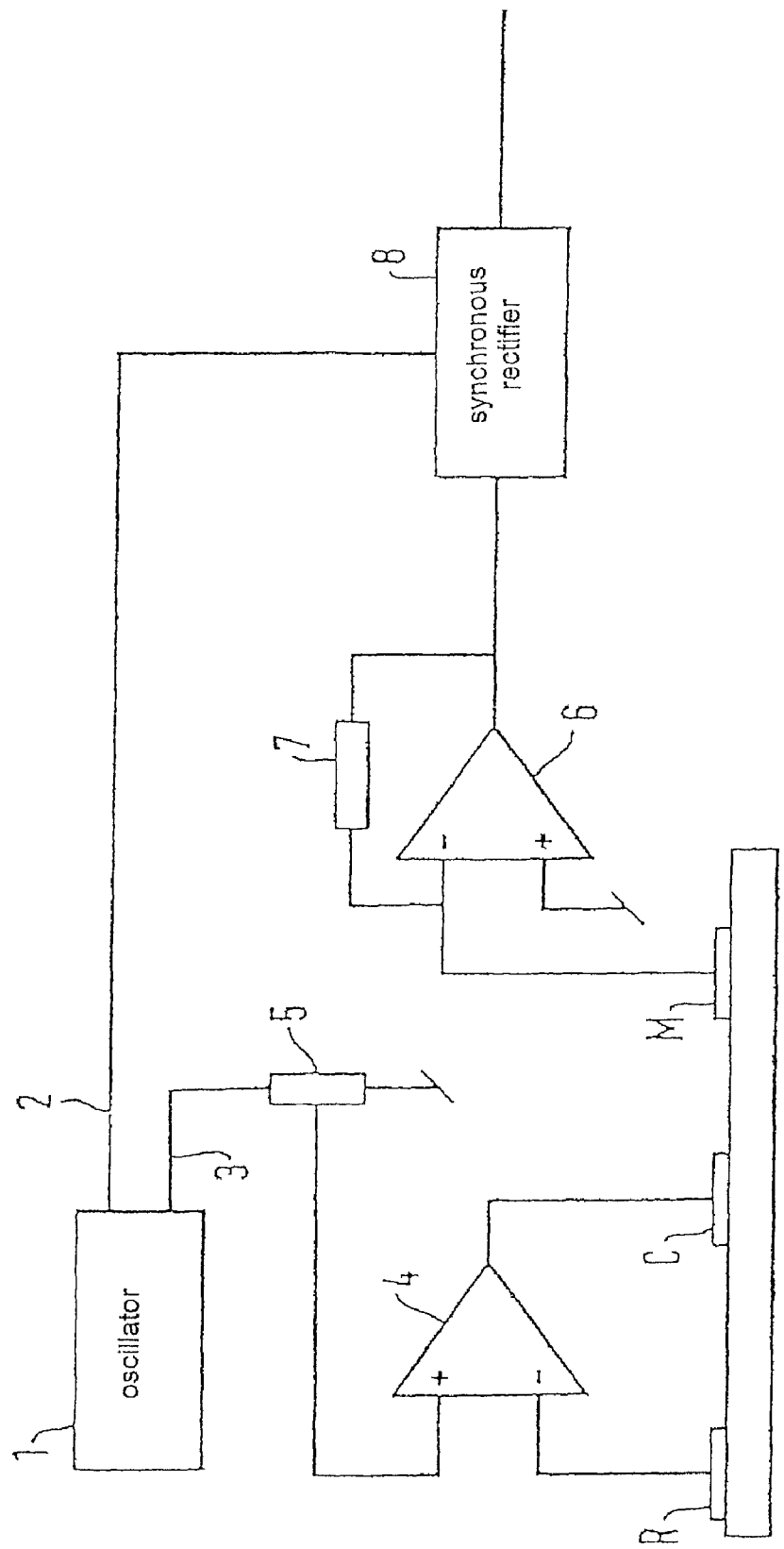
FIG. 7 illustrates a circuit of a skin impedance measurement device for measuring skin impedance, according to one or more embodiments of the present invention.

FIG. 7 is a block diagram for the apparatus according to an embodiment. It comprises a quadrature oscillator 1 whose output voltage frequency is preferably in the range 10-1000 Hz. A sine output 3 of the oscillator 1 is connected to a variable resistor 5, while a cosine output 2 of the oscillator 1 is connected to the reference input of a synchronous rectifier 8. The apparatus comprises three electrodes R, C and M. The principle of such a three-electrode system is described in Grimnes S., "Impedance measurement of individual skin surface electrodes", Med. & Biol. Eng. & Computing, vol. 21, 1983, pp. 750-55 and in Martinsen .O slashed . . G., Grimnes S., and Karlsen J., "An instrument for the evaluation of skin hydration by electrical admittance measurement", Innovation et Technologie en Biologie et Medecine, vol. 14, no. 5, 1993, pp. 588-96.

The R-electrode is connected to an inverting input and the C-electrode to the output of an operational amplifier 4 whose non-inverting input is connected to the variable resistor 5 and thereby the sine voltage output 3 of the oscillator 1. The variable resistor 5 determines the amplitude of the measuring voltage. The R- and C-electrodes may be short-circuited, i.e. connected with each other without affecting the operations of the apparatus. The M-electrode is connected to the inverting input of a transresistance amplifier 6 whose output is connected to the input of the synchronous rectifier 8. A feedback resistor 7 is connected in parallel between the transresistance amplifier's inverting input and its output.

Also, the R, C, and M electrodes of the sensor measuring skin impedance according to one or more embodiments of the present invention may be embodied in various shapes capable of maximizing the cross-section of the electrodes in contact with the skin, for example when the electrodes are miniaturized.

According to the sensor and method for measuring skin impedance of one or more embodiments of the present invention, accuracy in measuring skin impedance may be improved because an M electrode is slightly recessed with respect to an R electrode and a C electrode, and therefore, the M electrode may make contact with a user's skin after the R electrode and the C electrode make contact with the skin.

According to the sensor measuring skin impedance of one or more embodiments of the present invention, skin impedance may be easily and accurately measured by establishing an elastic element or a seesaw arm member to support any one of an R electrode, a C electrode or and an M electrode.

Although a few embodiments of one or more embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A sensor measuring skin impedance, the sensor comprising:
   a reference (R) electrode and a current carrying (C) electrode; and
   a measuring (M) electrode, recessed with respect to the R electrode and the C electrode, to measure impedance for a current flowing between the R electrode and the C electrode, across a skin surface contacted by the M electrode after the R electrode and the C electrode, wherein the M electrode is connected to an inverting input of a transresistance amplifier whose output is connected to an input of a synchronous rectifier.

2. The sensor of claim 1, wherein the M electrode is positioned between the R electrode and the C electrode, and the recess enables the M electrode to make contact with the skin surface after the R electrode and the C electrode.

3. The sensor of claim 1, wherein the R electrode, the C electrode and the M electrode are bar shaped.

4. A sensor measuring skin impedance, the sensor comprising:
   an R electrode connected to an inverting input of an operational amplifier;
   a C electrode to make contact with skin and connected to an output of the operational amplifier;
   an elastic element connected to the R electrode and the C electrode, the elastic element to compress according to a pressure exerted upon the R electrode and the C electrode; and
   an M electrode, recessed with respect to the R electrode and the C electrode, to measure impedance for a current flowing between the R electrode and the C electrode, across the skin, wherein the M electrode is connected to an inverting input of a transresistance amplifier whose output is connected to an input of a synchronous rectifier.

5. The sensor of claim 4, wherein the M electrode is located between the R electrode and the C electrode.

6. The sensor of claim 4, wherein the recess of the M electrode with respect to the R electrode and the C electrode falls within a range of 1 mm to 2 mm.

7. The sensor of claim 4, wherein the R electrode, the C electrode and the M electrode are bar shaped.

8. A sensor measuring skin impedance, the sensor comprising:
- an R electrode and a C electrode to make contact with a skin;
- an M electrode, recessed with respect to the R electrode and the C electrode; and
- a seesaw arm member to connect to the R electrode, the C electrode, and the M electrode,
- wherein the seesaw arm member includes a first elastic element connected to the R electrode and the C electrode to perform an elastic movement according to displacement of the R electrode and the C electrode and a second elastic element, connected to the M electrode, to perform an elastic movement according to displacement of the first elastic element, to enable the R electrode and the C electrode to make contact with the skin before the M electrode makes contact with the skin.

9. The sensor of claim 8, wherein the M electrode is located between the R electrode and the C electrode.

10. The sensor of claim 9, wherein the seesaw arm member to cause the M electrode to make contact with the user's skin after the R electrode and the C electrode.

11. The sensor of claim 8, wherein the R electrode, the C electrode and the M electrode are bar shaped.

12. A sensor measuring skin impedance, the sensor comprising:
- an R electrode and a C electrode to make contact with a user's skin;
- an M electrode, recessed with respect to the R electrode and the C electrode, wherein the M electrode is connected to an inverting input of a transresistance amplifier whose output is connected to an input of a synchronous rectifier; and
- an elastic element connected to the R electrode and the C electrode, the elastic element being compressed when pressure is applied to the R electrode and the C electrode, the compression causing the M electrode to no longer be recessed with respect to the R electrode and the C electrode, enabling the M electrode to make contact with the user's skin after the R electrode and the C electrode.

13. The sensor of claim 12, wherein the R electrode, the C electrode and the M electrode are bar shaped.

* * * * *